US006972196B1

(12) United States Patent
Mrksich et al.

(10) Patent No.: US 6,972,196 B1
(45) Date of Patent: Dec. 6, 2005

(54) MAKING SURFACES INERT BY MODIFYING WITH ALKANETHIOLATES

(75) Inventors: Milan Mrksich, Chicago, IL (US); Yan-Yeung Luk, Chicago, IL (US)

(73) Assignee: Arch Development Corporation, Chicago, IL (US)

( * ) Notice: Subject to any disclaimer, the term of this patent is extended or adjusted under 35 U.S.C. 154(b) by 453 days.

(21) Appl. No.: 09/689,263

(22) Filed: Oct. 11, 2000

(51) Int. Cl.$^7$ .................. C12N 5/06; C12N 5/08; C12N 11/14; C12N 11/02; C12Q 1/02
(52) U.S. Cl. .................. 435/395; 435/29; 435/176; 435/177; 435/180
(58) Field of Search .................. 435/174, 176, 435/177, 180, 29, 395; 530/402

(56) References Cited

FOREIGN PATENT DOCUMENTS

| | | |
|---|---|---|
| DE | P 3630184.1 | 12/1987 |
| JP | 06192058 | 12/1994 |

OTHER PUBLICATIONS

Chapman et al., J. Am. Chem. Soc. vol. 122, Aug 12, 200, pp. 8303–8304.*
Luk, Y.-Y.; Kato, M. and Mrksich, M.; "Self–assembled monolayers of alkanethiolates presenting mannitol groups are inert to protein adsorption and cell attachment"; *Langmuir* 2000, 16, 9604–9608, published Oct. 21, 2000.
Self–Assembled Monolayers of Alkanethiolates Presenting Mannitol Groups Are Inert to Protein Adsorption and Cell Attachment, Yan–Yeung Luk et al., Dept. of Chemistry, U. of Chicago, Jun. 29, 2000.
Borkholder, D.A., et al., "Microelectrode Arrays for Stimulation of Neural Slice Preparations", *J. Neurosci. Meth.*, 77, 61–66 (1997).
Chen, C. et al., "Geometric Control of Cell Life and Death", *Science*, 276, 1425–1428 (1997).
Deng, L. et al., "Self–Assembled Monolayers of Alkanethiolates Presenting Tri(propylene sulfoxide) Groups Resist the Adsorption of Protein", *J. Am. Chem. Soc.*, 118, 5136–5137 (1996).
Feldman, K. et al., "Probing Resistance to Protein Adsorption of Oligo(ethylene glycol)–Terminated Self–Assembled Monolayers by Scanning Force Microscopy", *J. Am. Chem. Soc.*, 121, 10134–10141 (1999).
Harder, P. et al., "Molecular Conformation in Oligo(ethylene glycol)–Terminated Self–Assembled Monolayers on Gold and Silver Surfaces Determines Their Ability to Resist Protein Adsorption", *J. Phys Chem B, 102*, 426–436 (1998).
Harris, J.M. *Poly(Ethyl Glycol) Chemistry*; Plenum: New York (1992).
Hodneland, C. et al., "Biomolecular Surfaces that Release Ligands Under Electrochemical Control", *J. Am. Chem. Soc.*, 22, 4235–4236 (2000).

Hodneland, C. et al., "Design of Self–Assembled Monolayers That Release Attached Groups Using Applied Electrical Potentials," *Langmuir, 13*, 6001–6003 (1997).
Houseman, B. et al., "The Role of Ligand Density in the Enzymatic Glycosylation of Carbohydrates Presented on Self–Assembled Monolayers of Alkanethiolates on Gold", *Angew. Chem. Int. Ed., 38*, 782–785 (1999).
Jeon, S.I. et al. "Protein–Surface Interactions in the Presence of Polyethylene Oxide", *J. Colloid Interface Sci, 142*, 159–166 (1991).
Jo, S. et al., "Surface Modification Using Silanated Poly(ethylene glycol)s", *Biomaterials, 21*, 605–616 (2000).
Kapur, R. et al., "Streamlining the Drug Discovery Process by Integrating Miniaturization, High Throughput Screening, High Content Screening, and Automation on the CellChip™ System", *Biomediation Microdevices, 2*, 99–109 (1999).
Mrksich, M. et al. "Biospecific Adsorption of Carbonic Anhydrase to Self–Assembled Monolayers of Alkanethiolates that Present Benzenesulfonamide Groups on Gold", *J. Am. Chem. Soc., 117*, 12009–12010 (1995).
Mrksich, M. et al., "Patterning Self–Assembled Monolayers Using Microcontact Printing: A New Technology for Biosensors?", *Tibtech, 13*, 228–235 (1995).

(Continued)

*Primary Examiner*—David M. Naff
(74) *Attorney, Agent, or Firm*—Brinks Hofer Gilson & Lione

(57) ABSTRACT

Alkanethiols of formula (1) and the enantiomers of the alkanethiol of formula (1):

HS-L-Q-T    (1), and disulfides of formula (3) and the enantiomers of the disulfide of formula (3):

T-Q-L S-S-J    (3), where -T is a moiety of formula (2)

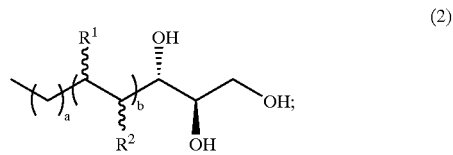

(2)

$R^1$ and $R^2$ are each individually selected from the group consisting of H and OH; a is 0 to 3; b is 0 to 3; and ∿∿∿ indicates that the chirality of the carbon atom to which it is attached is either R or S; may form inert surfaces that prevent the unwanted adsorption of proteins and cells.

31 Claims, 3 Drawing Sheets

OTHER PUBLICATIONS

Mrksich, M. "Tailored Substrates for Studies of Attached Cell Culture", *Cell Mol. Life Sci.,* 54, 653–662 (1998).

Mrksich, M. et al., "Surface Plasmon Resonance Permits in Situ Measurement of Protein Adsorption on Self–Assembled Monolayers of Alkanethiolates on Gold", *Langmuir,* 11, 4383–4385 (1995).

Mrksich, M. et al., "Using Microcontact Printing to Pattern the Attachment of Mammalian Cells to Self–Assembled Monolayers of Alkanethiolates on Transparent Films of Gold and Silver", *Experimental Cell Research,* 235, 305–313 (1997).

Mrksich, M. et al., "Using Self–Assembled Monolayers That Present Oligo(ethylene glycol) Groups to Control the Interactions of Proteins with Surfaces", *Am. Chem. Soc.,* 680, 361–373 (1997).

Mrksich, M. et al., "Using Self–Assembled Monolayers to Understand the Interactions of Man–Made Surfaces With Protein and Cells", *Annu, Rev. Biophys. Biomol. Structure.* 25, 55–78 (1996).

Murphy, E.F. et al., "The Reduced Adsorption of Proteins at the Phosphoryl Choline Incorporated Polymer–Water Interface", *Langmuir,* 15, 1313–1322 (1999).

Pertsin, A.J. et al., "Low–Energy Configurations of Methoxy Triethylene Glycol Terminated Alkanethiol Self–Assembled Monolayers and Their Relevance to Protein Adsorption", *J. Phys. Chem. B.,* 102, 4918–4926 (1998).

Prime, K.L. et al., "Adsorption of Proteins onto Surfaces Containing End–Attached Oligo(ethylene oxide): A Model System Using Self–Assembled Monolayers", *J. Am. Chem. Soc.,* 115, 10714–10721 (1993).

Prime, K.L. et al., "Self–Assembled Organic Monolayers: Model Systems for Studying Adsorption of Proteins at Surfaces", *Science,* 252, 1164–1167 (1991).

Saneinejad, S. et al., "Patterned Glass Surface Direct Cell Adhesion and Process Outgrowth of Primary Neurons of the Central Nervous System", *J. Biomed. Mater. Res.,* 42, 13–19 (1998).

Sigal, G.B. et al., "Effect of Surface Wettability on the Adsorption of Proteins and Detergents", *J. Am. Chem. Soc.,* 120, 3464–3473 (1998).

Sigal, G.B. et al., "Using Surface Plasmon Resonance Spectroscopy to Measure the Association of Detergents with Self–Assembled Monolayers of Hexadecanethiolate on Gold", *Langmuir,* 13, 2749–2755 (1997).

Spnke, J. et al., "Molecular Recognition at Self–Assembled Monolayers: Optimization of Surface Functionalization", *J. Chem. Phys.,* 99, 7012–7019 (1993).

Taunton, H. et al., "Forces Between Surfaces Bearing Terminally Anchored Polymer Chains in Good Solvents", *Nature,* 332, 712–714 (1988).

Wieland, B. et al., "Electrochemical and Infrared Spectroscopic Quantitative Determination of the Platinum–Catalyzed Ethylene Glycol Oxidation Mechanism at CO Adsorption Potentials", *Langmuir,* 12, 2594–2601 (1996).

Yousaf, M. et al., "Diels–Alder Reaction for the Selective Immobilization of Protein to Electroactive Self–Assembled Monolayers", *J. Am. Chem. Soc.,* 121, 4286–4287 (1999).

* cited by examiner

MAKING SURFACES INERT BY MODIFYING WITH ALKANETHIOLATES

FEDERALLY SPONSORED RESEARCH OR DEVELOPMENT

The subject matter of this application was in part funded by the DARPA and the NIH (Grant no. OM-R29-54621-04). The government may have certain rights in this invention.

BACKGROUND

The present invention relates to self-assembled monolayers (SAMs) of alkanethiolates.

SAMs of alkanethiolates on gold are an important class of model substrates for mechanistic studies of the interactions of proteins and cells with surfaces. A primary reason for the importance of these model substrates is the availability of SAMs that are inert—that is, SAMs that prevent or inhibit the adsorption of protein and the attachment of cells. Monolayers terminated in short oligomers of the ethylene glycol group ($[OCH_2CH_2]_nOH$, n=3–6) are known to prevent the adsorption of virtually all proteins under a wide range of conditions. This class of SAMs has been critical for developing methods to pattern the adhesion of cells, to prepare surfaces that present ligands for selective interactions with proteins, and to design electroactive dynamic substrates that can modulate the selective recognition of proteins.

Given the importance of inert surfaces, it is surprising that there are so few functional groups that have been identified that render materials inert—and none that are as effective at preventing protein adsorption as are oligo(ethylene glycol) groups when presented on SAMs. A monolayer presenting a tri(propylene sulfoxide) group was reported as inert to protein adsorption and cell attachment. While monolayers terminated in this propylene sulfoxide group prevented protein adsorption, they were generally less effective and less stable over time than were SAMs presenting oligo (ethylene glycol) groups. The synthetic route to the propylene sulfoxide oligomers is laborious, which further limits the utility of these monolayers. Another example, a monolayer terminated in the carbohydrate maltose, was reported to prevent protein adsorption. In that work, the lack of adsorption was demonstrated with ellipsometric measurements, which required the substrate be removed from solution, rinsed and then dried prior to the measurement. Because this and related ex situ techniques cannot detect weak and reversible adsorption, it is not clear whether these monolayers will ultimately prove inert in settings where the substrate is in contact with a protein-containing solution for long periods of time.

The development or identification of alternative functional groups that can render SAMs inert to protein adsorption and cell attachment is important, since it is probable that no one surface chemistry will be best suited to give an inert interface under all conditions. The availability of several inert surface chemistries would permit optimization of the substrate properties for each unique application.

BRIEF SUMMARY

In a first aspect, the present invention is an alkanethiol of formula (1) and the enantimomers of the alkanethiol of formula (1):

$$\text{HS-L-Q-T} \quad (1)$$

where -L- is $-(A_x\text{-}B_y\text{-}E_z\text{-}D_w\text{-}$; each A, B, E and D are individually $C(R_AR_A')—$, $—C(R_BR_B')—$, $—C(R_ER_E')—$, and $—C(R_DR_D')—$, respectively; each $R_A$, $R_B$, $R_E$ and $R_D$ are individually H, or any two of $R_A$, $R_B$, $R_E$ and $R_D$ together form a bond, or $R_A$, $R_B$, $R_E$ and $R_D$ together with the atoms to which they are bonded form a six-membered aromatic ring; each $R_A'$, $R_B'$, $R_E'$ and $R_D'$ are individually H, or any two of $R_A'$, $R_B'$, $R_E'$ and $R_D'$ together form a bond, or $R_A'$, $R_B'$, $R_E'$ and $R_D'$ together with the atoms to which they are bonded form a six-membered aromatic ring; each x, y and z are individually either 0 or 1; w is 1 to 5; -Q- is selected from the group consisting of

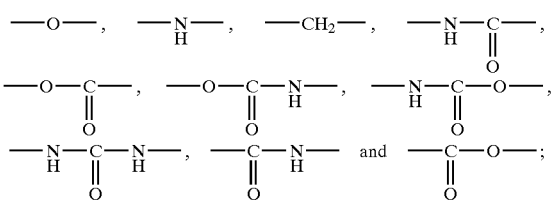

T is a moeity of formula (2)

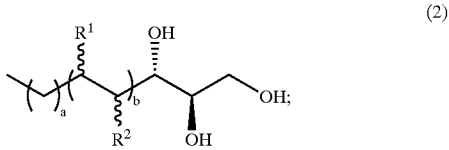

$R^1$ and $R^2$ are each individually selected from the group consisting of H and OH; a is 0 to 3; b is 0 to 3; and indicates that the chirality of the carbon atom to which it is attached is either R or S.

In a second aspect, the present invention is a disulfide of formula (3) and the enantiomers of the disulfide of formula (3)

$$\text{T-Q-L-S—S-J} \quad (3)$$

where -L-, -Q-, and -T have the same meaning as above; -J is selected from the group consisting of H, halogen, R, —OR, —NRR', —C(O)R, and —C(O)OR; R is selected from the group consisting of alkyl, alkenyl, alkynyl, aryl and heterocyclic radical; and R' is selected from the group consisting of H, alkyl, alkenyl, alkynyl, aryl and heterocyclic radical.

In a third aspect, the present invention is a substrate, includes (i) a surface layer comprising gold, and (ii) a plurality of moieties, on at least a portion of the surface layer, where the moieties are alkanethiolate moieties of formula (5) and enantiomers of the alkanethiolate moieties of formula (5):

$$\text{Surf-L-Q-T} \quad (5);$$

-L-, -Q-, and -T have the same meaning as above; and Surf designates where the moiety attaches to the surface.

In a fourth aspect, the present invention is a substrate, including (i) a surface layer comprising gold, and (ii) a monolayer comprising moieties, on at least a portion of the surface layer, where the moieties are alkanethiolate moieties; and the monolayer does not fail a cell patterning test at 25 days.

In a fifth aspect, the present invention is a cell chip, including a substrate described above, and cells on the substrate.

In a sixth aspect, the present invention is a protein chip, including a substrate described above, and protein on the substrate.

DEFINITIONS

"Alkyl" (or alkyl- or alk-) refers to a substituted or unsubstituted, straight, branched or cyclic hydrocarbon chain, preferably containing from 1 to 20 carbon atoms. More preferred alkyl groups are alkyl groups containing from 7 to 16 carbon atoms. Preferred cycloalkyls have from 3 to 10, preferably 3–6, carbon atoms in their ring structure. Suitable examples of unsubstituted alkyl groups include methyl, ethyl, propyl, isopropyl, cyclopropyl, butyl, isobutyl, tert-butyl, sec-butyl, cyclobutyl, pentyl, cyclopentyl, hexyl, cyclohexyl, and the like. "Alkylaryl" and "alkylheterocyclic" groups are alkyl groups covalently bonded to an aryl or heterocyclic group, respectively.

"Alkenyl" refers to a substituted or unsubstituted, straight, branched or cyclic, unsaturated hydrocarbon chain that contains at least one double bond, and preferably 2 to 20, more preferably 7 to 16, carbon atoms. Exemplary unsubstituted alkenyl groups include ethenyl (or vinyl)(—CH=CH$_2$), 1-propenyl, 2-propenyl (or allyl)(—CH2—CH=CH$_2$), 1,3-butadienyl (—CH=CHCH=CH$_2$), 1-butenyl (—CH=CHCH$_2$CH$_3$), hexenyl, pentenyl, 1,3,5-hexatrienyl, and the like. Preferred cycloalkenyl groups contain five to eight carbon atoms and at least one double bond. Examples of cycloalkenyl groups include cyclohexadienyl, cyclohexenyl, cyclopentenyl, cycloheptenyl, cyclooctenyl, cyclohexadienyl, cycloheptadienyl, cyclooctatrienyl and the like.

"Alkynyl" refers to a substituted or unsubstituted, straight, branched or cyclic unsaturated hydrocarbon chain containing at least one triple bond, and preferably 2 to 20, more preferably 7 to 16, carbon atoms. "Aryl" refers to any monovalent aromatic carbocyclic or heteroaromatic group, preferably of 3 to 10 carbon atoms. The aryl group can be monocyclic (i.e. phenyl (or Ph)) or polycyclic (i.e. naphthyl) and can be unsubstituted or substituted. Preferred aryl groups include phenyl, naphthyl, furyl, thienyl, pyridyl, indolyl, quinolinyl or isoquinolinyl.

"Halogen" (or halo-) refers to fluorine, chlorine, iodine or bromine. The preferred halogen is fluorine or chlorine.

"Heterocyclic radical" refers to a stable, saturated, partially unsaturated, or aromatic ring, preferably containing 5 to 10, more preferably 5 or 6, atoms. The ring can be substituted 1 or more times (preferably 1, 2, 3, 4 or 5 times) with a substituent. The ring can be mono-, bi- or polycyclic. The heterocyclic group consists of carbon atoms and from 1 to 3 heteroatoms independently selected from the group consisting of nitrogen, oxygen, and sulfur. The heteroatoms can be protected or unprotected. Examples of useful heterocyclic groups include substituted or unsubstituted, protected or unprotected acridine, benzathiazoline, benzimidazole, benzofuran, benzothiophene, benzothiazole, benzothiophenyl, carbazole, cinnoline, furan, imidazole, 1H-indazole, indole, isoindole, isoquinoline, isothiazole, morpholine, oxazole (i.e. 1,2,3-oxadiazole), phenazine, phenothiazine, phenoxazine, phthalazine, piperazine, pteridine, purine, pyrazine, pyrazole, pyridazine, pyridine, pyrimidine, pyrrole, quinazoline, quinoline, quinoxaline, thiazole, 1,3,4-thiadiazole, thiophene, 1,3,5-triazines, triazole (i.e. 1,2,3-triazole), and the like.

"Substituted" means that the moiety contains at least one, preferably 1–3 substituent(s). Suitable substituents include hydrogen (H) and hydroxyl (—OH), amino (—NH$_2$), oxy (—O—), carbonyl (—CO—), thiol, alkyl, alkenyl, alkynyl, alkoxy, halo, nitrile, nitro, aryl and heterocyclic groups. These substituents can optionally be further substituted with 1–3 substituents. Examples of substituted substituents include carboxamide, alkylmercapto, alkylsulphonyl, alkylamino, dialkylamino, carboxylate, alkoxycarbonyl, alkylaryl, aralkyl, alkylheterocyclic, and the like.

"Disulfide" means a compound containing a bond between two sulfur atoms.

"Alkanethiol" means a compound containing an alkyl group bonded to an SH group.

"Alkanethiolate" means a moiety corresponding to an alkanethiol without the hydrogen of the SH group.

"Alkylene" refers to a substituted or unsubstituted, straight, branched or cyclic hydrocarbon chain, preferably containing from 1 to 20 carbon atoms. More preferred alkylene groups are lower alkylene groups, i.e., alkylene groups containing from 1 to 6 carbon atoms. Preferred cycloalkylenes have from 3 to 10, preferably 3–6, carbon atoms in their ring structure. Suitable examples of unsubstituted alkylene groups include methylene, —(CH$_2$)$_n$—, —CH$_2$—CH(CH$_3$)—, —(C$_6$H$_{10}$)— where the carbon atoms form a six-membered ring, and the like.

All other acronyms and abbreviations have the corresponding meaning as published in journals relative to the art of chemistry.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein.

DETAILED DESCRIPTION

Figure 1:
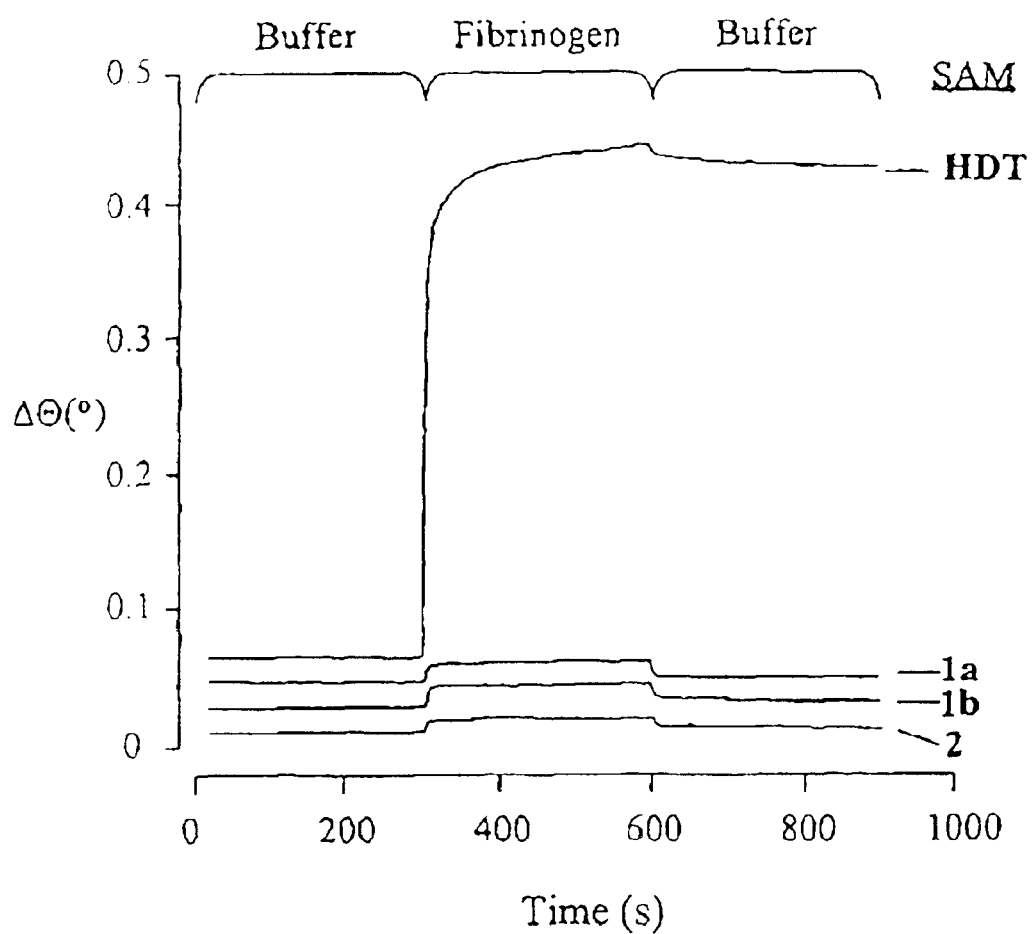
FIG. 1 illustrates data from surface plasmon resonance spectroscopy for the adsorption of fibrinogen to each of four SAMs, showing the relative change in angle of minimum reflectivity as sloutions are flowed over the SAMs. The curves are offset vertically for clarity.

The present invention includes new alkanethiols and disulfides, and SAMs prepared from these compounds that are inert surfaces. The SAMs exhibit excellent inertness to both protein adhesion and cell attachment, demonstrating their usefulness to prepare protein and cell chips.

The alkanethiols have the structure shown in formula (1) and the enantiomers of the structure shown in formula (1):

HS-L-Q-T             (1)

where -L- is -(A$_x$-B$_y$-E$_z$-D)$_w$-; each A, B, E and D are individually C(R$_A$R$_A$')—, —C(R$_B$R$_B$')—, —C(R$_E$R$_E$')—, and —C(R$_D$R$_D$')—, respectively; each R$_A$, R$_B$, R$_E$ and R$_D$ are individually H, or any two of R$_A$, R$_B$, R$_E$ and R$_D$ together form a bond, or R$_A$, R$_B$, R$_E$ and R$_D$ together with the atoms to which they are bonded form a six-membered aromatic ring; each R$_A$', R$_B$', R$_E$' and R$_D$' are individually H, or any two of R$_A$', R$_B$', R$_E$' and R$_D$' together form a bond, or R$_A$', R$_B$', R$_E$' and R$_D$' together with the atoms to which they are bonded form a six-membered aromatic ring; each x, y and z are individually either 0 or 1; and w is 1 to 5;

-Q- is selected from the group consisting of

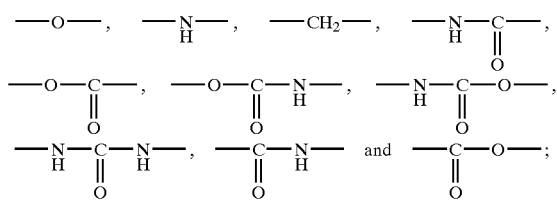

-T is a moiety of formula (2)

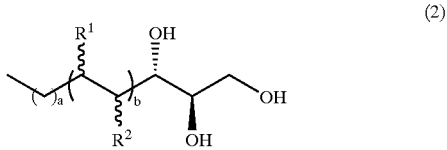
(2)

where $R^1$ and $R^2$ are each individually selected from the group consisting of H and OH; a is 0 to 3; b is 0 to 3; and ⁓ indicates that the chirality of the carbon atom to which it is attached may be either R or S.

The disulfides have the structure shown in formula (3) and the enantiomers of the structure shown in formula (3):

T-Q-L S-S-J (3)

where -L-, -Q- and -T have the same meaning as in formula (1), and -J is selected from the group consisting of H, halogen, R, —OR, —NRR', —C(O)R, and —C(O)OR; R is selected from the group consisting of alkyl, alkenyl, alkynyl, aryl and heterocyclic radical; R' is selected from the group consisting of H, alkyl, alkenyl, alkynyl, aryl and heterocyclic radical.

Preferably, -L- contains 6 to 20 carbon atoms, more preferably 8 to 18 carbon atoms. Preferably, -L- contains 1 or 0 double bonds, or 1 triple bond. Most preferably, -L- is an alkylene containing 6 to 18 carbon atoms.

Preferably, -Q- is —O— or —CH$_2$—.

Preferably, -T is a moiety of formula (2')

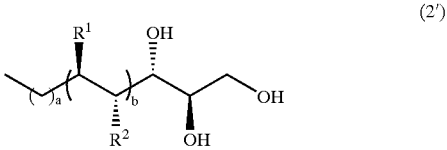
(2')

Most preferably a is 1, b is 1 and at least one of $R^1$ and $R^2$ is OH.

Preferably, -J is a moiety of formula (4)

-L'-Q'-T' (4), an alkyl having 1 to 4 carbon atoms, or is —(CH$_2$)$_c$(OCH$_2$CH$_2$)$_n$OH; where -L'-, -Q'-, and -T' have the same meaning as -L-, -Q-, and -T respectively, c is 2 to 20, and n is 1 to 3. Most preferably -J is moiety of formula (4'):

L-Q-T (4').

The alkanethiols and disulfides of the present invention may be synthesized using reagents and reaction well known to those of ordinary skill in the art, such as those described in "Advanced Organic Chemistry" J. March (Wiley & Sons, 1994); and "Organic Chemistry" 4th ed., Morrison and Boyd (Allyn and Bacon, Inc., 1983). For example, the following reaction scheme may be used:

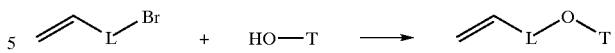

Further photolysis with thioacetic acid and AIBN (2,2'-azobisisobutyronitrile) in THF (tetrahydrofuran) forms the thioester of the alkanethiol of formula (1). Hydrolysis then gives alkanethiols of formula (1) with -Q- being —O—. Optionally, —OH groups in -T may be protected using acetone, and deprotection may take place before, after, or during hydrolysis of the thioester. For alkanethiols of formula (1) where -Q- is —NH—, Br in the above reaction scheme above may be replaced with NH$_2$, and the OH may be converted to a tosylate or mesylate. For alkanethiols of formula (1) where -Q- is —CH$_2$—, the OH may be converted to a tosylate or mesylate, and Br converted to the corresponding Grignard. For alkanethiols of formula (1) where -Q- is —CO—O—, Br in the above reaction scheme may be replaced with CO$_2$H. For alkanethiols of formula (1) where -Q- is —O—CO—, Br in the above reaction scheme may be replaced with OH, and the OH may be converted to the corresponding acid. For alkanethiols of formula (1) where -Q- is —NH—CO—, Br in the above reaction scheme may be replaced with NH$_2$, and the OH may be converted to the corresponding acid. For alkanethiols of formula (1) where -Q- is —CONH—, Br in the above reaction scheme may be replaced with CO$_2$H, and the OH may be converted to the corresponding primary amine (for example, by tosylation or mesylation followed by reaction with ammonia). For alkanethiols of formula (1) where -Q- is —NH—CO—NH—, Br in the above reaction scheme may be replaced with NH$_2$, and the OH may be converted to the corresponding isocyanate. For alkanethiols of formula (1) where -Q- is —NH—CO—O—, Br in the above reaction scheme may be replaced with —N=C=O to give an isocyanate, which is then reacted with the hydroxyl as shown. Similarly, the disulfides may be formed by first forming alkanethiols, followed by oxidative coupling. When the disulfide is not symmetric, two different alkanethiols are oxidized together.

When applied to a surface containing gold, the alkanethiols and disulfides will form SAMs. In the case of the alkanethiols, the hydrogen is lost, and the remaining moiety attaches to the surface through the sulfur atom. In the case of the disulfides, the disulfide bridge is broken, and the remaining moieties attach to the surface through the sulfur atoms. The surface preferably has a plurality of alkanethiolate moieties shown in formula (5)

Surf-S-L-Q-T (5)

where -L-, -Q- and -T have the same meaning as in formula (1), and Surf designates where the moiety attaches to the surface. The density of moieties on the surface is typically $10^{10} \pm 5\%$ per square centimeter. The moieties of the present invention may cover the entire surface, or may be patterned on the surface. Patterning may be carried out by, for example, by microprinting, as described in Mrksich, M.; Dike, L. E.; Tien, J.; Ingber, D. E.; Whitesides, G. M., *Experimental Cell Research* 1997 235, 305–313; Chen, C. S.; Mrksich, M.; Huang, S.; Whitesides, G. M.; Ingber, D. E., *Science* 1997, 276, 1425–1428; and Mrksich, M.; Whitesides, G. M., *TIBTECH.* 1995, 13, 228–235.

Preferably the surface contains gold, more preferably the surface contains 50 to 100 atom percent gold. Preferably, the surface is pure or fine gold, or an alloy of gold with copper, silver, or a combination thereof.

The surface may be on a base. The base may have the same composition as the surface (for example a gold surface on a gold plate), or the surface may be, for example, a film, foil, sheet, or plate, on a base having a different composition. The base may be any material, such as metal, ceramic, plastic, or a natural material such as wood. Examples of bases include glass, quartz, silicon, transparent plastic, aluminum, carbon, polyethylene and polypropylene.

The surface material may be attached to the base by any of a variety of methods. For example, a film of the surface material may be applied to the base by sputtering or evaporation. If the surface material is a foil or sheet, in could be attached with an adhesive. Furthermore, the surface need not completely cover the base, but may cover only a portion of the base, or may form a pattern on the base. For example, portions of the base could be patterned by sputtering the base, covering those portions of the base where no surface material is desired. These patterns may include an array of regions containing, or missing, the surface material.

Figure 3:
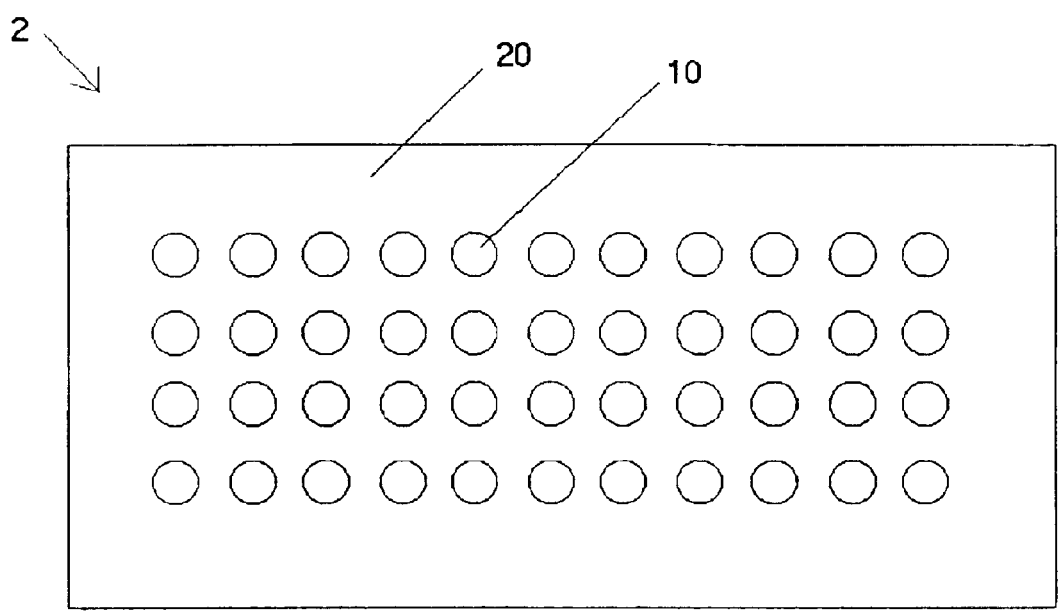
FIG. 3 illustrates a patterned substrate.
Figure 4:
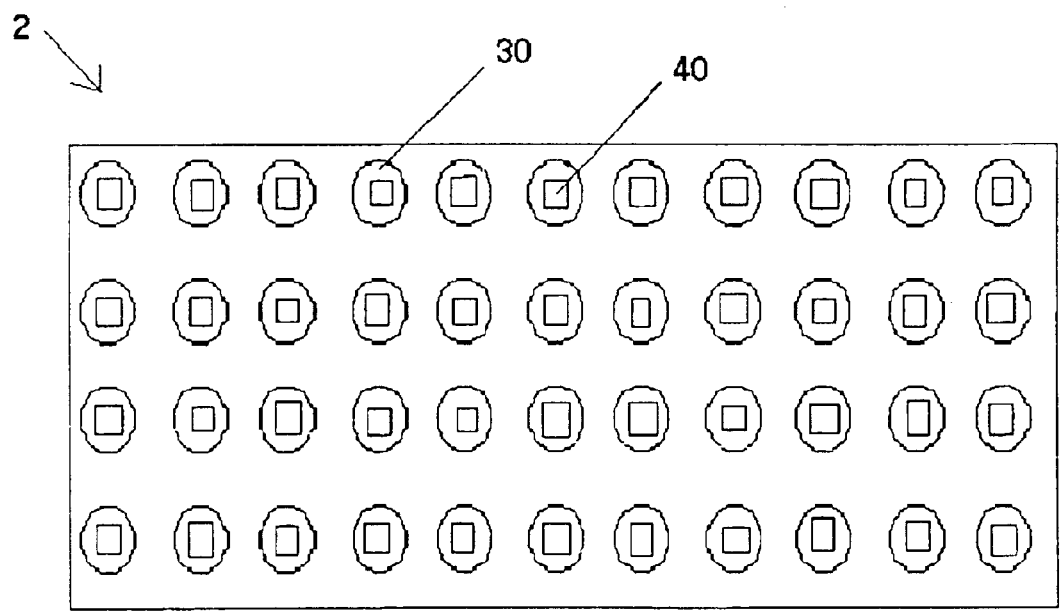
FIG. 4 illustrates another patterned substrate.

A cell chip is an array of regions containing cells on a surface, separated by regions containing no cells or cells at a much lower density. Since the SAMs of the present invention are inert, it is difficult for cells to attach. A cell chip may be prepared by applying SAMs of the present invention on regions of the surface that are to remain free of cells (or is intended to have cells at a lower density). The remaining regions could be left uncovered, or could be cover with SAMs that are not inert. For example, FIG. 3 illustrates one possible pattern, where circles 10 contain a SAM of hexadecanethiolate, and the remainder 20 of the surface is covered with a SAM of the present invention, all on a surface 2. Another example, FIG. 4 illustrates another possible pattern, where squares 30 contain a SAM of hexadecanethiolate, and regions 40 surrounding the squares contain a SAM of the present invention, all on a surface 2.

Once the surface is patterned as desired, the cells may be allowed to attach and proliferate in the regions not containing SAMs of the present invention, by contacting those regions with cells, and providing the nutrients and conditions necessary for the cells to proliferate.

One measure of the inertness of a surface is the number of day needed to fail a cell pattern test. A cell pattern test is carried out as follows: A surface is patterned into hydrophobic regions of hexadecanethiolate (HDT) and surrounded by the inert monolayer to be tested. The pattern is formed by microprinting. Albino 3T3-Swiss fibroblasts (American Type Culture Collection) are harvested from culture dishes with trypsin-EDTA, washed, and resuspended in DMEM (Dulbecco's Modification of Eagle's Medium) supplemented with 10% fetal bovine serum. The suspended cells are added to wells (10,000/well) containing patterned surfaces immersed in DMEM supplemented with serum. Serum-supplemented medium is exchanged with fresh medium after 12 hours and then every 5 days. Cell cultures are maintained at 37° C. and photographed daily. When the density of the cells in the test region is equal to or great than the density in the regions of hexadecanethiolate, the test is failed. Preferably, SAMs of the present invention do not fail the cell patterning test at 12 days, more preferably at 14 days, even more preferably at 25 days.

A protein chip is an array of regions containing protein, separated by regions containing no protein or protein at a much lower density. Since the SAMs of the present invention are inert, it is difficult for proteins to attach. In the same manner as a cell chip may be prepared, a protein chip may be prepared by applying SAMs of the present invention on regions of the surface that are to remain free of protein (or intended to have protein at a lower density). The remaining regions could be left uncovered, or could be cover with SAMs that are not inert The same variety of patterns is possible with protein chips as described above for cell chips; FIGS. 3 and 4 are two possible patterns. The protein chip may then be prepared by contacting the surface with the desired protein or proteins.

Alternatively, a protein chip may be formed by covering both regions of the surface that are intended to have protein, and those that are not intended to have protein, with SAMs of the present invention. Those regions that are intended to have protein will also include an alkanethiolate corresponding to an alkanethiol terminated in a specific moiety. The protein to be attached is chosen to include a region that will capture the specific moiety, anchoring the protein to the chosen regions. For example, the specific moiety may be the conjugate of glutathione and benzoquinone of formula (6)

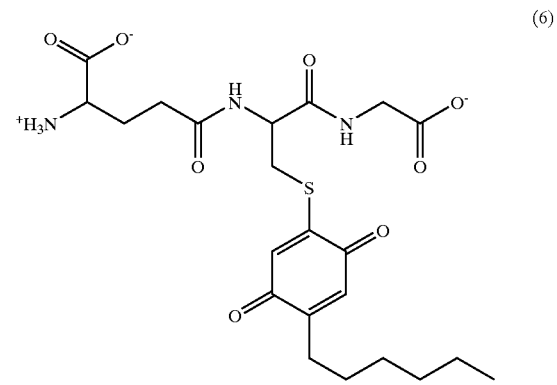

(6)

and the protein may be a fusion protein of a protein of interest (such as the peptide hemagglutinin (HA) and glutathione S-transferase (GST) (the fusion protein being designated as GST-HA). When this fusion protein encounters the alkanethiolate terminating in the conjugate, the protein is cross-linked to the alkanethiolate, anchoring the protein in place. Since the SAM mostly contains the inert moiety of the present invention, other undesired proteins do not attach to the surface.

GST is commonly used as an affinity handle for the purification of recombinant proteins; the protein is expressed and purified as the GST fusion protein, and then treated with a protease to remove the GST domain (see, for example, Smith, D. B.; Johnson, K. S. Gene 1988, 67, 31). These fusion proteins could be used without synthetic modification to form protein chips. An additional benefit of using GST fusion proteins together with SAMs formed from alkanethiols terminated with the conjugate of formula (6) is that the reactivity of the surface towards immobilization could be controlled electrochemically, by way of reversible reduction of the quinone of formula (6) to the unreactive hydroquinone.

EXAMPLES

Two experimental procedures were used to evaluate the monolayers as inert surfaces. Surface plasmon resonance (SPR) spectroscopy measures the adsorption of protein to the monolayer. All SPR experiments were performed on a BIAcore 1000 instrument. Substrates were glued into plastic BIACore cassettes with a two-part epoxy (DEVCON). Phosphate-buffered saline (PBS; 10 mM phosphate, 150 mM sodium chloride, pH 7.6) was degassed under vacuum and all protein solutions were filtered through 0.45-$\mu$m filters before use. SPR is well suited for characterization of protein adsorption because it measures adsorption in situ and can detect weak, readily reversible protein adsorption. For all monolayers, a panel of five proteins that spanned a range in molecular weight and pi were investigated.

In a second set of experiments, the ability of the monolayers to pattern the long-term adhesion of albino Swiss 3T3 fibroblast cells was investigated. These experiments used monolayers that are patterned into hydrophobic regions of hexadecanethiolate (HDT) and surrounded by the inert monolayer. Cells initially attach only to the hydrophobic regions and proliferate to completely fill those regions after 2–3 days in culture. The periods of time that the cells remain confined to the pattern were compared—because the surrounding monolayer prevents attachment—to assess the effectiveness of the inert monolayer. The cell patterning experiments impose a more demanding environment than do the protein adsorption experiments, and hence, provide a more stringent test of inertness.

Protein adsorption and cell attachment on four different monolayers was compared. Gold films were prepared by evaporation of titanium (1.5 nm) and then gold (40 nm) onto glass cover slips (0.20 mm, No. 2, Corning). The SAMs were prepared by immersing gold films of approximately 1 cm² in ethanolic solutions of alkanethiol (2 mM) for 9 hours. The SAMs were rinsed with ethanol and dried with nitrogen before use. As a control monolayer that is not inert, a SAM of hexadecanethiolate that presents hydrophobic methyl groups at the surface were used. Monolayers terminated in the tri(ethylene glycol) group were used as the current standard for inert surfaces. Each of the two additional monolayers presents the mannitol group and differs only in the length of alkyl chain to which the mannitol group is appended.

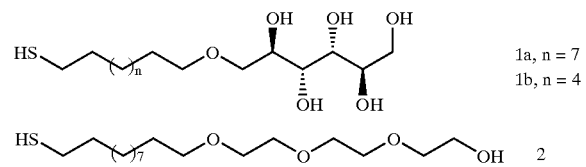

Alkanethiol 1a has an alkyl chain of eleven methylene units, which is the standard length in SAMs that are used in bio-interfacial science. Alkanethiol 1b has three fewer methylene units in the alkyl chain. Alkanethiol 2 terminates in the tri(ethylene glycol) group.

The synthetic scheme for preparing 1a and 1b is shown below. The following conditions were employed in the synthesis: (a) NaH/DMF; (b) CH₃COSH, AIBN, hv, THF; (c) HCl/CH₃OH, reflux. The reactions all used distilled solvents and were performed under a nitrogen atmosphere.

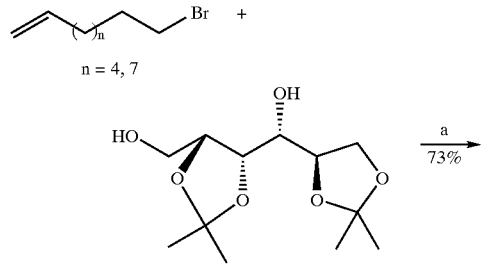

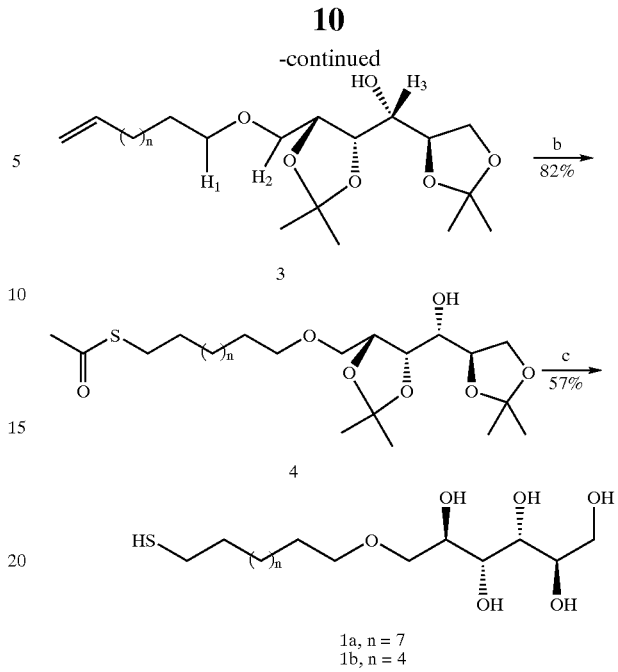

Dimethylketal 3. To a solution of 1,2:3,4-di-o-isopropylidene-D-mannitol (316 mg, 1.20 mmol) in DMF (10 ml) was added sodium hydride (30 mg, 60% dispersion in oil, 1.20 mmol). The solution was stirred for 10 min at room temperature and then 8-bromo-1-octene (220 mg, 1.20 mmol) was added over a period of 5 min. The solution was stirred for 12 hours and then concentrated in vacuo. The residue was purified by flash chromatography (1.5% CH₃OH/CH₂Cl₂) to give 330 mg (0.883 mmol, 73%) of 3 as a colorless oil: ¹H NMR (400 MHz, CDCl₃) δ 5.82–5.72 (m, 1H), 4.92 (q, J=10.2, 2H), 4.41–4.30 (m, 2H), 4.12–3.95 (m, 3H), 3.77–3.65 (m, 2H), 3.13 (d, J=6.16, 1H), 2.00 (q, J=7.1, 2H), 1.53 (s, 3H), 1.42 (s, 3H), 1.40 (s, 3H), 1.37 (s, 3H), 1.18 (m, 6H).

Thioester 4. A solution of 2 (151 mg, 0.41 mmol), thiol acetic acid (91 mg, 1.2 mmol) and AIBN (80 mg, 0.487 mmol) in THF (15 ml) was irradiated with UV light (RAYONET PHOTOCHEMICAL REACTOR LAMP) in a photochemical reactor for 5 hours with stirring. The solution was concentrated in vacuo and the residue was purified by flash chromatography (1% CH₃OH/CH₂Cl₂) to give 147 mg (0.328 mmol, 82%) of 4 as a colorless oil: ¹H NMR (400 MHz, CDCl₃) δ 4.41–4.30 (m, 2H), 4.12–3.95 (m, 3H), 3.77–3.65 (m, 2H), 3.57–3.47 (m, 3H), 3.14–3.12 (d, J=6.16, 1H), 2.90–2.85 (t; J=7.38, 2H), 2.33 (s, 3H), 1.64–1.55 (m, 4H), 1.53 (s, 3H), 1.42 (s, 3H), 1.40 (s, 3H), 1.37 (s, 3H), 1.41 (m, 6H).

Alkanethiol 1b. To a solution of 4 (147 mg, 0.328 mmol) in methanol (15 ml) was added 5 drops of 12 N HCl. The solution was refluxed for 8 hours, cooled, and concentrated in vacuo. The residue was purified by recrystallization from methanol to give 61 mg (0.187 mmol, 57 %) of 1b as a white solid: ¹H NMR (400 MHz, CD₃OD) δ 3.85–3.59 (m, 6H), 3.58–3.46 (m, 4H), 2.52–2.45 (t, 2H), 1.64–1.55 (m, 4H), 1.45–1.28 (m, 8H).

Alkanethiol 1a. The mannitol-terminated alkanethiol 1a was synthesized with the same protocol starting with 11-bromo-1-undecene in place of 8-bromo-1-octene.

SPR was used to measure the adsorption of five proteins—fibrinogen, pepsin, lysozyme, insulin, and trypsin—to the four monolayers. SPR measures changes in the refractive index of a solution near the interface with a gold film by measuring changes in the angle ($\Delta\Theta_m$) at which p-polarized light reflected from the glass/gold interface has a minimum in intensity. SAMs were mounted in a flow cell and experiments were performed by first flowing a phosphate buffered saline (PBS) through the cell for 5 minutes, then a solution of protein in the same buffer (0.5 mg/ml) for 5 minutes, and then PBS for 5 minutes. The rise in $\Delta\Theta_m$ upon introduction of the protein solution has two contributions. The first is due to the increase in refractive index of the solution caused by the dissolved protein—the "bulk effect"—and does not represent protein adsorption. The second contribution is due to the adsorption of protein to the SAM. The amount of protein that adsorbs irreversibly to the SAM is determined by comparing the shift in $\Theta m$ before and after the SAM is exposed to protein. An increase in $\Theta m$ of 0.10 corresponds to an increase in density of adsorbed protein of 1 ng/mm$^2$.

FIG. 1 shows data for the adsorption of fibrinogen to the four SAMS. A complete monolayer of protein adsorbs to the SAM of hexadecanethiolate. The change in $\Theta_m$ of 0.35° corresponds to a density of protein of 3,500 pg/mm$^2$. The two monolayers presenting mannitol groups, by contrast, show essentially no adsorption of fibrinogen. This lack of adsorption is indistinguishable from that on monolayers presenting tri(ethylene glycol) groups. Experiments with the four other proteins gave similar results and demonstrated that the mannitol group is broadly effective at preventing protein adsorption, as shown in Table 1. For all five proteins, the amount of irreversible adsorption was less than 2% of the total amount that adsorbed on the methyl-terminated SAMs (HDT).

TABLE 1

Adsorption of Protein on Monolayers.

| SAM | Thickness[a] | Fibrinogen[b] 340 kD,[d] 5.5[e] | Pepsin 35 kD, < 1 | Lysozyme 14 kD, 1.4 | Insulin 5.4 kD, 5.4 | Trypsin 24 kD, 10.5 |
|---|---|---|---|---|---|---|
| 1a | 18.0 Å | 27[c] | <10 | 19 | 15 | <10 |
| 1b | 15.7 Å | 45 | 12 | 10 | 25 | 16 |
| 2 | 19.5 Å | 29 | <10 | <10 | <10 | <10 |
| HDT | 20.0 Å | 3,432 | 1,337 | 1,023 | 688 | 661 |

[a]Thickness of the SAM measured by ellipsometry (±0.5 Å).
[b]All protein solutions were 0.5 mg/ml in PBS (10 mM phosphate, 150 mM sodium chloride, pH 7.6).
[c]The amount of protein that remains adsorbed to the SAM was determined by SPR and is reported in the units of pg/mm$^2$. Each value of absorbed protein was taken from a single experiment and have a variance of approximately 5% across independent experiments.
[d]Molecular weight of the protein.
[e]p/ of the protein.

The degree to which these monolayers could prevent the adhesion and growth of cells that were confined to a patterned substrate was evaluated. Gold films were patterned by microcontact printing a set of circular regions of hexadecanethiolate that were 200 μm in diameter and then the films were immersed in a solution of 1a, 1b or 2 to assemble an inert monolayer on the non-printed areas. Albino 3T3-Swiss fibroblasts (American Type Culture Collection) were harvested from culture dishes with trypsin-EDTA, washed, and resuspended in DMEM supplemented with 10% fetal bovine serum. The suspended cells were added to wells (10,000/well) containing patterned substrates immersed in DMEM supplemented with serum. Serum-supplemented medium was exchanged with fresh medium after 12 hours and then every 5 days. Cell cultures were maintained at 37° C. and photographed daily. When the suspension of cells was added to culture wells containing the substrates, cells attached only to the methyl-terminated regions. For each of the substrates patterned with the inert monolayers (1a, 1b and 2), cells spread and proliferated to completely occupy these regions but did not invade the surrounding inert regions. The period of time that cells remain confined to the patterned monolayers provides a relative measure of the effectiveness of inert surface chemistries, and a direct measure for identifying inert surfaces that are most effective for applications requiring long-term cell patterning.

Figure 2:
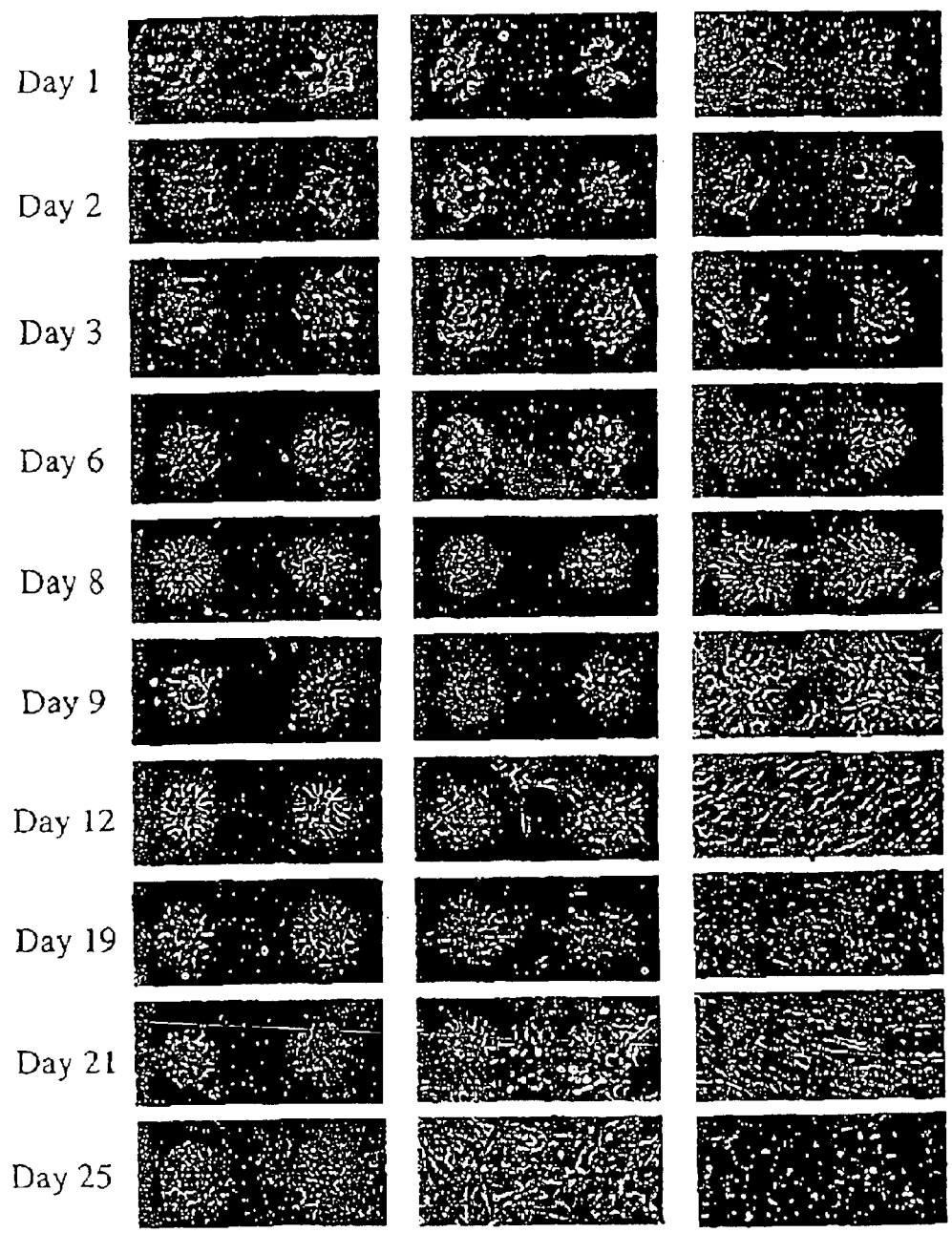
FIG. 2 is optical micrographs for cells patterned into circular regions of HDT surrounded by regions of other SAMs.

Albino 3T3-Swiss fibroblast cells patterned on the monolayers were kept at 37° C. in serum-containing media for four weeks. The media was exchanged every five days and cells were photographed daily, as shown in FIG. 2. In all cases, cells remained patterned to the circular regions of hexadecanethiolate for at least six days in culture. The tri(ethylene glycol)-terminated (prepared from alkanethiol 2) monolayers began to fail after seven days, with cells spreading onto the inert regions. After 12 days, cells had migrated from the circular regions and divided to give a confluent monolayer of cells, with a complete loss of pattern. Monolayers terminated in the mannitol group (prepared from alkanethiol 1a) were substantially more effective at confining cells for longer periods. Even after 21 days, cells remained completely confined to the patterns. After 25 days in culture, the viability of the adherent cells decreased, and therefore prevented an assessment of the monolayer over longer periods of time. Monolayers that presented the mannitol group on the shorter polymethylene chain (prepared from alkanethiol 1b) were also more effective than monolayers presenting the tri(ethylene glycol) group, but were not as effective as monolayers of 1a. Monolayers of 1b generally failed at two weeks in culture. These long-term patterning experiments were repeated on three separate occasions with consistent results: monolayers of 2 fail at approximately one week, monolayers of 1b fail at approximately two weeks and monolayers of 1a are effective for at least three weeks.

The SAMs 1a and 1b are highly effective as inert surfaces. SPR showed that monolayers of 1a and 1b prevented the adsorption of several different proteins, including the "sticky" protein fibrinogen. In this respect, the monolayers were indistinguishable from monolayers presenting tri(ethylene glycol) groups, which are the current standard for inert model surfaces. When evaluated for the ability to maintain the patterned adhesion of cells, it was found that SAMs of 1a were superior to SAMs presenting tri(ethylene glycol) groups. In this and other work, it has been found that SAMs presenting tri(ethylene glycol) groups fail at approximately seven days in culture. The SAMs of the present invention, by contrast, maintained the pattern of adherent cells over as many as 25 days.

A reaction scheme to prepare an alkanethiol terminated in a moiety that will cross-link to a glutathione S-transferase fusion protein (alkanethiol (Z)) is described below. In the reaction scheme, hydroquinone was protected as the bistetrahydropyranyl ether, which was then deprotonated with tert-butyl lithium and alkylated with 1,4-dibromobutane. Separately, molecule (Y) was prepared by protecting the tri(ethylene glycol)-terminated alkanethiol as the tritylthioether. The free hydroxyl group of this molecule was alkylated with (X) to give the conjugate. Deprotection of the tetrahydropyranyl ethers with pyridinium para-toluene sulfate revealed the hydroquinone, which was then oxidized with ammonium cerium nitrate to give the corresponding benzoquinone. Michael addition of the cysteine thiol of glutathione to the quinone resulted in the final precursor, which was treated with trifluoroacetic acid to remove the trityl protecting group.

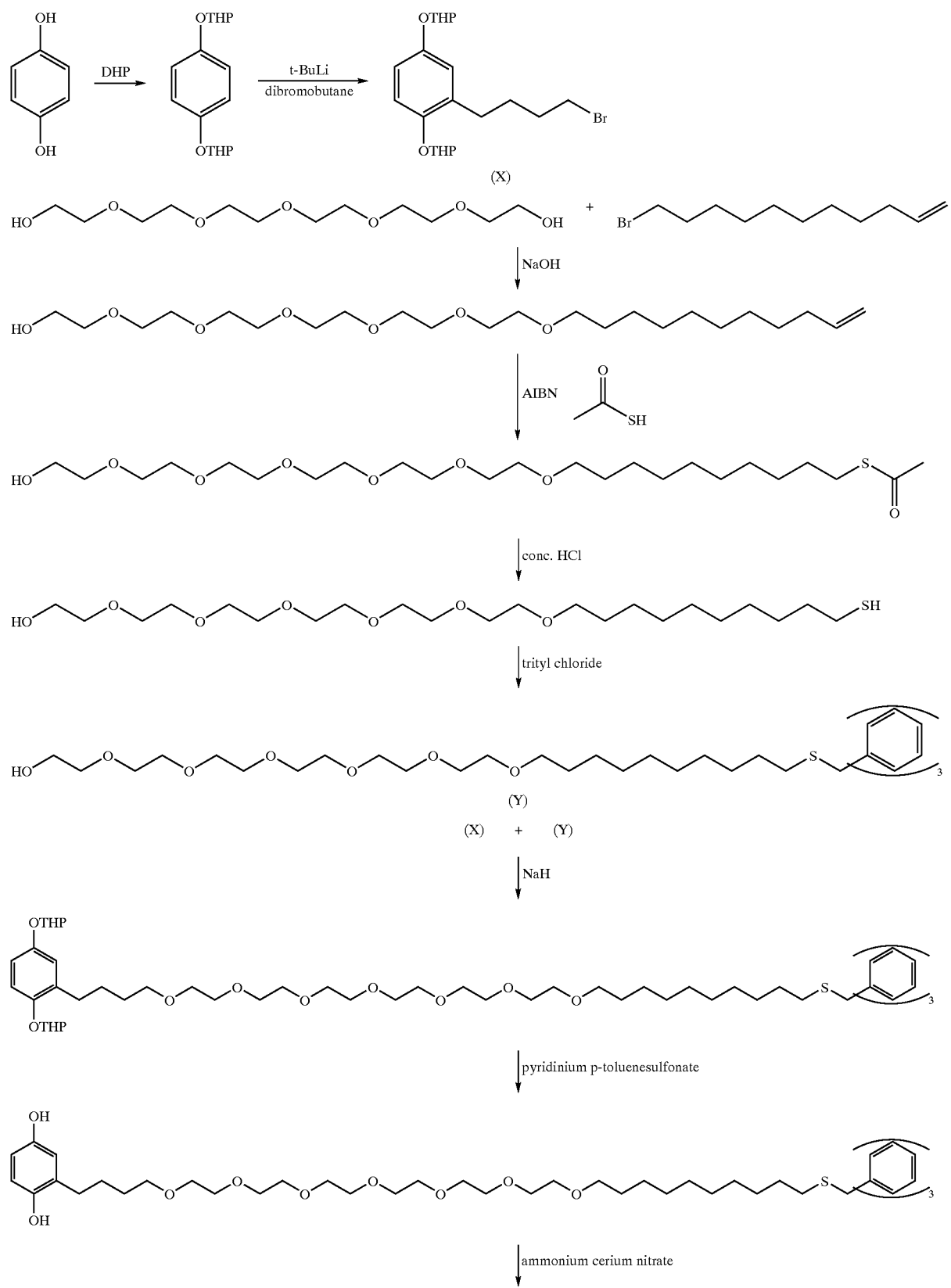

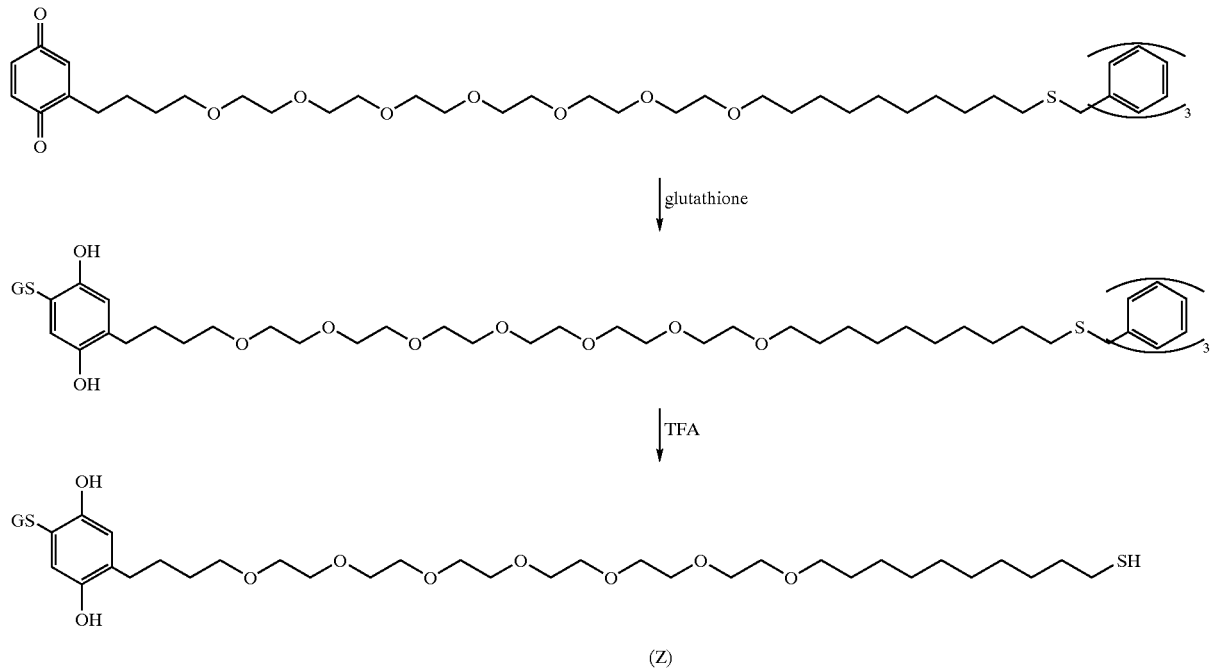

A monolayer was prepared from a mixture of alkanethiol (Z) and a alkanethiol 1a (in a ratio of 1:99). The surface was treated to oxidize the hydroquinone group of alkanethiol (Z) to the corresponding benzoquinone, either by applied electrical potentials (+500 mV for 1 minute), or by treatment with a chemical oxidant (for example, with a substituted quinone). Surface plasmon resonance (SPR) spectroscopy was used to characterize the immobilization of GST-HA fusion protein to this monolayer. We used GST-HA as a model system because an antibody against this peptide is available. In these experiments, phosphate buffered saline (pH 7.4) was flowed over the monolayer for 2 minutes to establish a baseline. A solution of GST-HA (100 $\mu$M) in the same buffer was then flowed over the monolayer for 15 minutes to observe binding. Finally the protein solution was replaced with buffer for 5 minutes to quantitate the amount of protein that was irreversibly immobilized. The GST-HA was efficiently immobilized to the monolayer and the anti-HA antibody bound to the immobilized peptide. This antibody did not bind, however, to monolayers to which only GST had been immobilized, demonstrating the biospecificity that is afforded with the inert SAMs of the present invention.

The SAMs of the present invention are significant because they extend the time course over which cells can be patterned in culture. This enhancement is important for several applications that use cells as functional components. A primary example is the use of genetically engineered cells for screening libraries of drug candidates. This and other applications require substrates that can maintain patterned cell populations with excellent fidelity and over long periods of time. Furthermore, the SAMs of the present invention are highly effective at preventing protein adsorption and extend the times over which cultured cells can be maintained in patterns.

Obviously, numerous modifications and variations of the present invention are possible in light of the above teachings. It is therefore to be understood that within the scope of the appended claims, the invention may be practiced otherwise than as specifically described herein.

What is claimed is:

1. A substrate, comprising:
   (i) a surface layer comprising gold, and
   (ii) a monolayer comprising moieties, on at least a portion of said surface layer,
   wherein said moieties are alkanethiolate moieties; and
   said monolayer does not fail a cell patterning test at 12 days, wherein said test is failed when the density of cells in a test region containing the alkanethiolate moieties becomes equal to or greater than the density of cells in a region not containing the alkanethiolate moieties during culturing of said cells.

2. A cell chip, comprising:
   (A) the substrate of claim 1, and
   (B) cells, on said substrate.

3. A method of making a cell chip, comprising:
   contacting cells with the substrate of claim 1.

4. The method of claim 3, further comprising allowing said cells to proliferate.

5. A substrate, comprising:
   (i) a surface layer comprising gold, and
   (ii) a plurality of moieties, on at least a portion of said surface layer,
   wherein said moieties are alkanethiolate moieties of formula (5) or enantiomers of the alkanethiolate moieties of formula (5):

$$\text{Surf-S-L-Q-T} \qquad (5);$$

-L- is -A$_x$-B$_y$-E$_z$-D)$_w$-;
   each A, B, E and D are individually C(R$_A$R$_A$')—, —C(R$_B$R$_B$')—, —C(R$_E$R$_E$')—, and —C(R$_D$R$_D$')—, respectively;
   each R$_A$, R$_B$, R$_E$ and R$_D$ are individually H, or any two of R$_A$, R$_B$, R$_E$ and R$_D$ together form a bond, or R$_A$, R$_B$, R$_E$ and R$_D$ together with the atoms to which they are bonded form a six-membered aromatic ring;

each $R_A'$, $R_B'$, $R_E'$ and $R_D'$ are individually H, or any two of $R_A'$, $R_B'$, $R_E'$ and $R_D'$ together form a bond, or $R_A'$, $R_B'$, $R_E'$ and $R_D'$ together with the atoms to which they are bonded form a six-membered aromatic ring;

each x, y and z are individually either 0 or 1;

w is 1 to 5;

-Q- is selected from the group consisting of

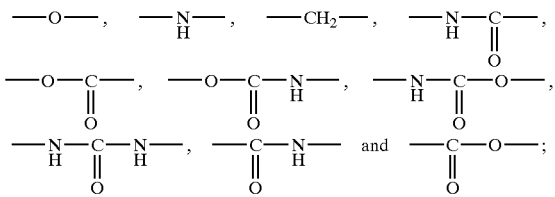

-T is a moiety of formula (2)

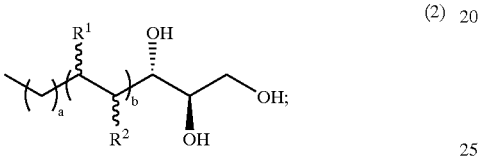

$R^1$ and $R^2$ are each individually selected from the group consisting of H and OH;

a is 0 to 3;

b is 0 to 3;

∿∿∿ indicates that the chirality of the carbon atom to which it is attached is either R or S; and Surf designates where the moiety attaches to said surface.

6. The substrate of claim 5, further comprising:

(iii) a monolayer comprising said moieties, wherein said monolayer does not fail a cell patterning test at 12 days, wherein said test is failed when the density of cells in a test region containing the alkanethiolate moieties becomes equal to or greater than the density of cells in a region not containing the alkanethiolate moieties during culturing of said cells.

7. The substrate of claim 5, further comprising:

(iv) a base, wherein said surface layer is on said base.

8. The substrate of claim 7, wherein -T is a moiety of formula (2')

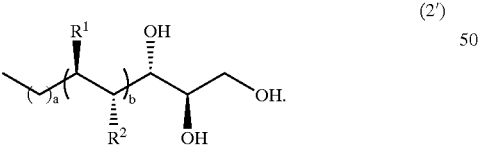

9. The substrate of claim 8, wherein a is 1, b is 1 and at least one of $R^1$ and $R^2$ is OH.

10. The substrate of claim 8, wherein -L- contains 8 to 18 carbon atoms.

11. The substrate of claim 10, wherein -L- contains 1 or 0 double bonds, or 1 triple bond.

12. The substrate of claim 8, wherein -L- is an alkylene containing 6 to 18 carbon atoms.

13. The substrate of claim 8, wherein -Q- is —O— or —CH$_2$—.

14. The substrate of claim 9, wherein -L- is an alkylene containing 6 to 18 carbon atoms, and -Q- is —O—.

15. A cell chip, comprising:
(A) the substrate of claim 5, and
(B) cells, on said substrate.

16. A cell chip, comprising:
(A) the substrate of claim 6, and
(B) cells, on said substrate.

17. A cell chip, comprising:
(A) the substrate of claim 8, and
(B) cells, on said substrate.

18. A cell chip, comprising:
(A) the substrate of claim 10, and
(B) cells, on said substrate.

19. A cell chip, comprising:
(A) the substrate of claim 12, and
(B) cells, on said substrate.

20. A cell chip, comprising:
(A) the substrate of claim 14, and
(B) cells, on said substrate.

21. A method of making a cell chip, comprising:
contacting cells with the substrate of claim 5.

22. The method of claim 21, further comprising allowing said cells to proliferate.

23. A method of making a cell chip, comprising:
contacting cells with the substrate of claim 6.

24. The method of claim 22, further comprising allowing said cells to proliferate.

25. A method of making a cell chip, comprising:
contacting cells with the substrate of claim 8.

26. The method of claim 25, further comprising allowing said cells to proliferate.

27. A method of making a cell chip, comprising:
contacting cells with the substrate of claim 14.

28. The method of claim 27, further comprising allowing said cells to proliferate.

29. A method of making a substrate, comprising contacting a surface with an alkanethiol of formula 1 or the enantiomers of formula (1);

HS-L-Q-T    (1), wherein -L- is -($A_x$-$B_y$-$E_z$-D)$_w$-;

each A, B, E and D are individually $C(R_AR_A')$—, —$C(R_BR_B')$—, —$C(R_ER_E')$—, and —$C(R_DR_D')$—, respectively;

each $R_A$, $R_B$, $R_E$ and $R_D$ are individually H, or any two of $R_A$, $R_B$, $R_E$ and $R_D$ together form a bond, or $R_A$, $R_B$, $R_E$ and $R_D$ together with the atoms to which they are bonded form a six-membered aromatic ring;

each $R_A'$, $R_B'$, $R_E'$ and $R_D'$ are individually H, or any two of $R_A'$, $R_B'$, $R_E'$ and $R_D'$ together form a bond, or $R_A'$, $R_B'$, $R_E'$ and $R_D'$ together with the atoms to which they are bonded form a six-membered aromatic ring;

each x, y and z are individually either 0 or 1;

w is 1 to 5;

-Q- is selected from the group consisting of

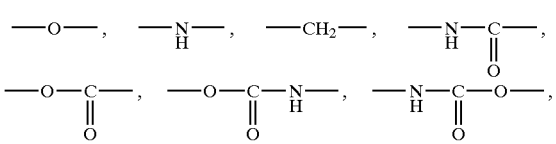

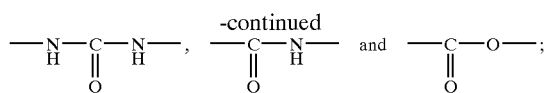

T is a moiety of formula (2)

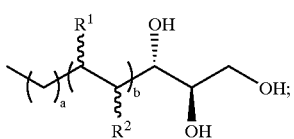

R¹ and R² are each individually selected from the group consisting of H and OH;

a is 0 to 3;

b is 0 to 3; and

⌇⌇⌇ indicates that the chirality of the carbon atom to which it is attached is either R or S;

wherein said surface comprises gold.

30. The method of claim 29, wherein -T is a moiety of formula (2')

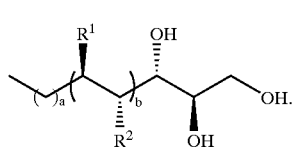

31. The method of claim 30 wherein a is 1, b is 1, at least one of R¹ and R² is OH, -L- is an alkylene containing 6 to 18 carbon atoms, and -Q- is —O—.

* * * * *

UNITED STATES PATENT AND TRADEMARK OFFICE
CERTIFICATE OF CORRECTION

PATENT NO. : 6,972,196 B1
DATED : December 6, 2005
INVENTOR(S) : Milan Mrksich et al.

It is certified that error appears in the above-identified patent and that said Letters Patent is hereby corrected as shown below:

Title page,
Item [56], References Cited, OTHER PUBLICATIONS,
"Hodneland, C. et al." reference, "22" should read -- 122 --;
"Spnke, J. et al." reference, should read -- Spinke, J. et al. --.

Signed and Sealed this

Fourteenth Day of March, 2006

JON W. DUDAS
*Director of the United States Patent and Trademark Office*